United States Patent [19]

Sprague

[11] 4,143,054
[45] Mar. 6, 1979

[54] 7-OXABICYCLOHEPTANE- AND 7-OXADICYCLOHEPTENE COMPOUNDS

[75] Inventor: Peter W. Sprague, Pennington, N.J.

[73] Assignee: E. R. Squibb & Sons, Inc., Princeton, N.J.

[21] Appl. No.: 848,543

[22] Filed: Nov. 4, 1977

[51] Int. Cl.$^2$ .................................... C07D 307/00
[52] U.S. Cl. .................. 260/346.22; 260/343.21; 260/343.3 R; 260/345.2; 260/346.71
[58] Field of Search ......................... 260/346.22

[56] References Cited

PUBLICATIONS

Hamberg et al., Proc. Nat. Acad. Sci. U.S.A. 70, 899–903 (1973).
Wlodawer et al., J. Am. Chem. Soc. 93, 2815–2816 (1971).
Corey et al., J. Am. Chem. Soc. 98, 6417–6418 (1976).
Bundy, Tetrahedron Letters, 24, 1957–1960 (1975).
Rose et al., Proc. Soc. Exp. Biol. and Med. 153, 209–212 (1976).

*Primary Examiner*—O
*Assistant Examiner*—Bernard Dentz

*Attorney, Agent, or Firm*—Lawrence S. Levinson; Merle J. Smith

[57] ABSTRACT

New 7-oxabicycloheptane- and 7-oxabicycloheptene compounds which have the general formula

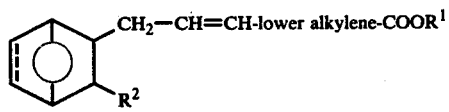

and intermediates therefor which have the general formulas

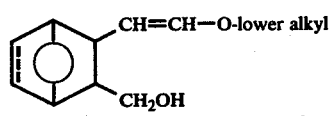

and

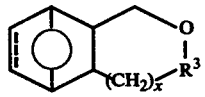

are useful as cardiovascular agents.

7 Claims, No Drawings

7-OXABICYCLOHEPTANE- AND 7-OXABICYCLOHEPTENE COMPOUNDS

SUMMARY OF THE INVENTION

This invention relates to a group of compounds of the PGH$_2$ type and intermediates therefor which are cardiovascular agents useful, for example, in the treatment of thrombolytic disease. These compounds have the structural formula

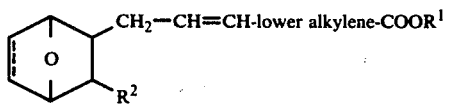

R$^1$ is hydrogen or lower alkyl;
R$^2$ is —CHO, CH$_2$OH or —CH=CH—R$^3$ -lower alkylene-CH$_3$; and R$^3$ is keto (C=O) or hydroxymethyl (CHOH).
The intermediates have the formulas

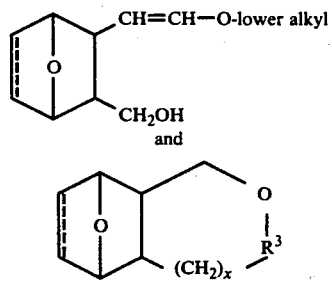

R$^3$ has the same meaning as above and x is 0 or 1.
The dotted line in each structural formula represents an optional double bond.

DETAILED DESCRIPTION OF THE INVENTION

The sequence of reactions described below yields a series of 7-oxabicycloheptane- and 7-oxabicycloheptene derivatives of the PGH$_2$ type.

Not only can members of the group be derived from other members and thus have utility as intermediates, but they also have physiological activity themselves.

Thus, when maleic anhydride is made to react with an unsubstituted or substituted furan having the formula

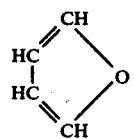

e.g., in ether solution at room temperature, this results in a compound having the formula

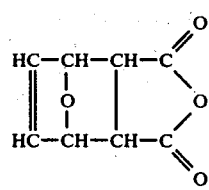

Reduction of the compound of formula V, e.g., catalytically, for example, in the presence of palladium-carbon, provides a reduced product having the formula

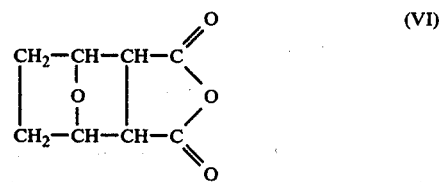

The compound of formula VI can then be converted to a compound having the formula

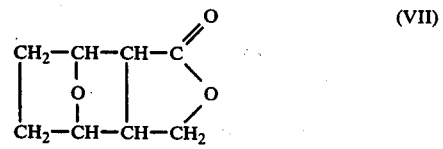

e.g., by reduction in tetrahydrofuran with a borohydride like sodium borohydride or zinc borohydride.

Treatment of the compound of formula VII with diisobutylaluminum hydride or diisobutylborane yields a compound having the formula

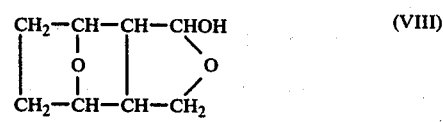

which then is submitted to Witting reaction conditions e.g., with an (alkoxymethyl)triphenylphosphonium halide like (methoxymethyl)triphenylphosphonium chloride in the presence of an alkali metal alkylamide like lithium diisopropylamide, a lithium alkyl like n-butyl lithium in an inert organic medium like toluene, tetrahydrofuran or the like, at a temperature in the range of about −10° to 25° C.

This reaction produces a compound having the formula

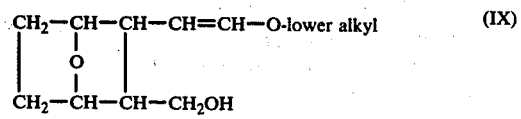

This product of formula IX is acylated, e.g., with an acylpyridinium halide like N-acetylpyridinium chloride in the presence of an acid acceptor like pyridine. oxidized with an oxidizing agent like mercuric acetate in an organic medium like tetrahydrofuran, then demetalated with a reducing agent like potassium iodide the yield a product having the formula

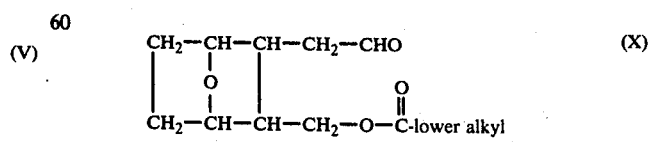

Alternatively, the product of formula IX can be treated with an acid like formic acid or trifluoroacetic acid to yield a product having the formula

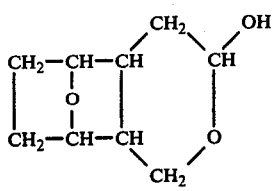

These products of formulas X or X1 are subjected to a Wittig reaction, e.g., with a carboxyalkyl triphenylphosphonium halide to obtain a product having the formula (XII)

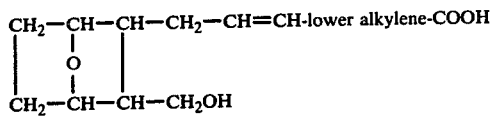

By esterifying the product of formula XII, e.g., with a diazoalkane like diazomethane in an inert organic solvent like ether or with a substituted diazoalkane like diphenyldiazomethane, the lower alkyl ester or substituted lower alkyl ester of that compound (i.e., $R^1$ is lower alkyl) is obtained.

The hydroxymethyl group in the 3-position of this ester is next oxidized, e.g., with chromium trioxide in pyridine, to obtain the aldehyde compound having the formula (XIII)

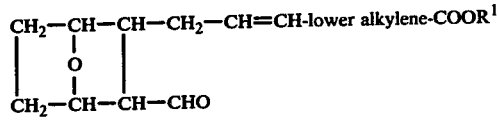

wherein $R^1$ is lower alkyl.

Subjecting the compound of formula XII to a Horner-Wittig reaction using an alpha ketophosphonate such as dimethyl 2-oxoheptylphosphonate and a base such as sodium hydride in an inert organic solvent such as dimethoxyethane or alternatively a Wittig reaction using an alpha keto phosphorus ylide such as tributyl or triphenyl 2-oxoheptylidine phosphorane in an organic solvent such as tetrahydrofuran provides a product having the formula (XIV)

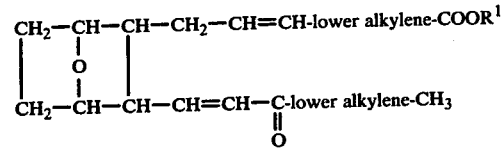

wherein $R^1$ is lower alkyl.

This product is then reduced, e.g., with lithium diisobutyl aluminum hydride, with zinc borohydride, sodium borohydride or sodium cyanoborohydride to yield a product having the formula

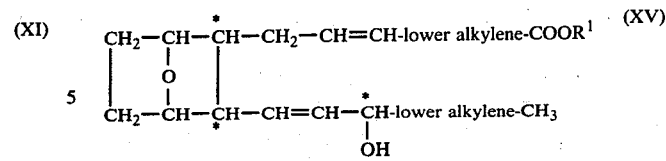

which can be converted to the free acid, i.e., a compound having the formula

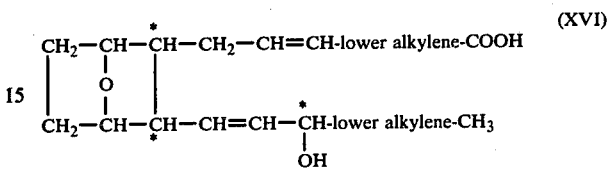

by treatment with a base such as lithium hydroxide followed by neutralization with an acid such as dilute hydrochloric acid.

If, instead of reacting maleic anhydride with the unsubstituted or substituted furan of formula IV, it is made to react with maleic acid, e.g., in water at room temperature, the unsaturated product having the formula

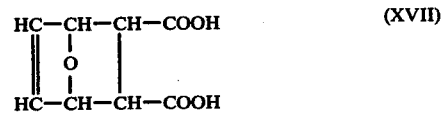

is obtained.

This can then be converted by reaction with an acid anhydride such as trifluoroacetic acid anhydride followed by treatment with a reducing agent such as sodium borohydride to the 5,6-unsaturated analog of a compound of formula VII above, i.e., a compound having the formula

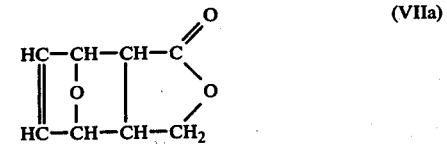

Starting with this compound instead of with the compound of formula VII and following the same sequence of steps as described above with respect to the latter compound and its successor compounds, there are obtained compounds corresponding to those of formulas VIII to XVI inclusive but having a double bond in the 5,6-position.

Additionally, the compound of formula VIIa can be reduced e.g., with hydrogen over palladium on carbon to obtain a compound of formula VII and this intermediate processed as described above.

The symbols in the foregoing formulas and throughout this specification have the meanings defined above. The lower alkyl and lower alkylene groups are straight or branched chain aliphatic hydrocarbon radicals having up to seven carbon atoms, e.g., methyl, ethyl, propyl, isopropyl, butyl, isobutyl, t-butyl, amyl and the like. The $C_1$-$C_4$ and especially the $C_3$-$C_4$ members are preferred.

Preferred compounds are compounds of formulas I, II and III wherein $R^1$ is hydrogen or lower alkyl, particularly $C_1$-$C_4$ lower alkyl and especially methyl, $R^2$ is —$CH_2OH$ or especially —$CH=CH$—$R^3$-lower alkylene-$CH_3$, particularly wherein the lower alkylene group has 3 or 4 carbons in a linear chain; and $R^3$ is hydroxymethyl. Compounds without the optional double bond are preferred over those with the double bond. Compounds of formula I, and especially those having the applicable foregoing characteristics, are preferred over compounds of formulas II and III. The products of the examples constitute preferred embodiments as well as provide additional experimental details and serve as models for additional members of the group.

The compounds of this invention have three centers of asymmetry as indicated by the asterisks in formulas XV and XVI. The various stereoisomeric forms are within the scope of the invention.

Thus when the first sequence of reactions described above are followed, i.e., reacting maleic anhydride with a furan of formula IV, compounds are obtained wherein both side chains, i.e., those residues attached to the 2 and 3 positions on the 7-oxabicyclo[2,2,1]heptane ring system, are cis to the 7-oxa bridge.

These can be shown by the common method of depicting steric structure as follows with respect to a compound of formula VIII, for example

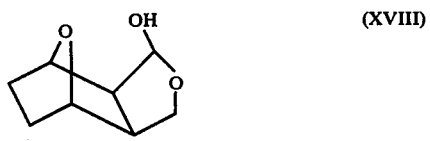
(XVIII)

the right hand ring being in the exo position. When the keto group in the side chain of the compound of formula XIV is reduced as first described above, a mixture of stereo-isomeric compounds in which the hydroxy group is either R ($\beta$) or S ($\alpha$) is usually obtained. They can be graphically described as follows:

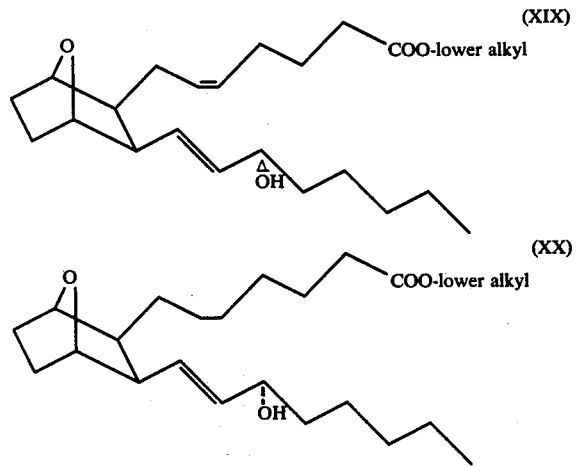

The same considerations apply to the acids which are obtained by hydrolysis. The stereoisomeric pairs can be resolved by conventional techniques, such as chromatography on silica gel.

On the other hand, when the alternate procedures described above are used, e.g., reacting a furan with maleic acid and optionally reducing the double bond, stereo-isomeric compounds are obtained wherein the lactole ring and subsequent compounds are in the endo position as depicted graphically with respect to a compound of formula XVIII:

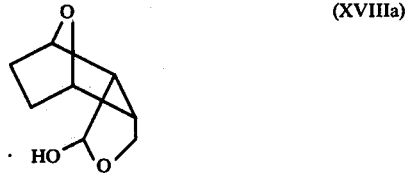

Additional experimental details are found in the examples which represent preferred embodiments.

The compounds of this invention are cardiovascular agents useful as platelet aggregation inhibitors e.g., for treatment of thrombolytic disease such as coronary or cerebral thromboses. They are also selective thromboxane $A_2$ synthetase inhibitors, e.g., having a vasodilatory effect for treatment of myocardial ischemic disease such as angina pectoris. They can be administered orally or parenterally to various mammalian species known to be subject to such maladies, e.g., cats, dogs, and the like in an effective amount within the dosage range of about 1 to 100 mg./kg., preferably about 1 to 50 mg./kg. and especially about 2 to 25 mg./kg. on a regimen in single or 2 to 4 divided daily doses.

The active substance can be utilized in a composition such as tablet, capsule, solution or suspension containing about 5 to about 500 mg. per unit of dosage of a compound or mixture of compounds of formula I. They may be compounded in conventional manner with a physiologically acceptable vehicle or carrier, excipient, binder, preservative, stabilizer, flavor, etc. as called for by accepted pharmaceutical practice. Also as indicated in the discussion above, certain members additionally serve as intermediates for other members of the group.

The following examples are illustrative of the invention. All temperatures are in degrees Celsius.

EXAMPLE 1

(Exo)Hexahydro-4,7-epoxyisobenzofuran-1,3-dione

A mixture containing 30.0 g. (0.18 mole) of 7-oxabicyclo[2.2.1]-5-heptene-2,3-dicarboxylic anhydride [Ber. 62, 554 (1929); Ann. 460, 98(1928)],1.5 g. of 5% Pd/C and 1.5 l. of ethyl acetate is hydrogenated in an atmospheric hydrogenator. The reaction is stopped after uptake of 4.518 l. of hydrogen. The catalyst is filtered from the reaction mixture and the solvent is stripped off under vacuum to yield 29.8 g. of (exo)hexahydro-4,7-epoxyisobenzofuran-1,3-dione, m.p. 112°–114°.

EXAMPLE 2

(Exo)Hexahydro-4,7-epoxyisobenzofuran-1(3H)-one

To a slurry of 6.7 g. (0.18 mole) of sodium borohydride in 50 ml. of dry tetrahydrofuran is added a solution of 29.8 g. (0.18 mole) of (exo)hexahydro-4,7-epoxyisobenzofuran-1,3-dione in 500 ml. of dry tetrahydrofuran over a 10 minute period with stirring and ice-bath cooling. The resulting mixture is stirred under nitrogen for 5 hours and then stripped of solvent under vacuum. The residue is treated with 100 ml. of 10% hydrochloric acid solution while being cooled in an ice-bath. The resulting slurry is extracted with dichloromethane (5×100 ml.), dried over sodium sulfate and concentrated to yield crystalline crude material. This is recrystallized from benzene-hexane to yield 20.1 g. of (exo)- hexahydro-4,7-epoxyisobenzofuran-1(3H)-one, m.p. 112°–118°.

EXAMPLE 3

(Exo)Octahydro-4,7-epoxyisobenzofuran-1-ol

A solution of (exo)hexahydro-4,7-epoxyisobenzofuran-1(3H)-one (3 g., 0.02 moles) in 100 ml. of anhydrous toluene is chilled to −78° and treated dropwise over ten minutes with a solution of diisobutyl aluminum hydride in toluene (1.5 molar, 26 ml., 0.04 moles). The resulting slurry is stirred at −78° for twenty minutes (a solution results). The reaction is quenched by adding dropwise 24 ml. of 10% acetic acid and allowing the reaction mixture to warm to room temperature. The mixture is then poured into 100 ml. of 10% hydrochloric acid saturated with sodium chloride. The product is exhaustively extracted with dichloromethane (8×100 ml.). The combined dichloromethane extracts are washed with 50 ml. of 5% sodium bicarbonate, dried over sodium sulfate, and concentrated in vacuo. The resultant crystalline product is recrystallized from benzene to yield 2.4 g. of (exo)octahydro-4,7-epoxyisobenzofuran-1-ol, m.p. 125°–127°.

EXAMPLE 4

(Exo)-3-(2-Methoxyethenyl)-7-oxabicyclo[2.2.1]heptane-2-methanol

A slurry of (methoxymethyl)-triphenylphosphonium chloride (123.47 g., 0.36 moles) in anhydrous toluene (1700 ml.) is chilled in an ice bath and treated dropwise over ten minutes with a solution of lithium diisopropylamide (38.6 g., 0.36 moles) in anhydrous tetrahydrofuran. The resulting red solution is stirred at 0° for ten minutes then treated via a solid addition device with (exo)octahydro-4,7-epoxyisobenzofuran-1-ol (18.7 g., 0.12 moles). The mixture is then stirred at room temperature for two hours. The mixture is poured into brine (1000 ml.) and treated with 10% hydrochloric acid to pH 6.8. The mixture is extracted several times with diethyl ether. The combined ether extracts are dried over sodium sulfate and concentrated in vacuo. The residue is dissolved in diethyl ether (500 ml.) and chilled overnight. The solid precipitate is filtered off and the filtrate concentrated in vacuo. The residue is chromatographed on silica gel (1500 ml.) eluting with (1) dichloromethane and (2) ethyl acetate. The crude product contained in the ethyl acetate fractions is distilled in vacuo to yield 14.5 g. of (exo)-3-(2-methoxyethenyl)-7-oxabicyclo[2.2.1]heptane-2-methanol, b.p. 100–105°/0.001 mm.

EXAMPLE 5

(Exo)Octahydro-5,8-epoxy-1H-benzopyran-3-ol (Exo)-3-(2-Methoxyethenyl)-7-oxabicyclo[2.2.1]heptane-2-methanol (10.2 g., 0.055 moles) is dissolved in cold 88% formic acid (166 ml.) at 0° then left stirring without cooling under nitrogen for thirty minutes. The reaction mixture is then chilled in an ice bath and treated dropwise over forty-five minutes with 10% sodium hydroxide to pH 7.5. The solution is saturated with sodium chloride and extracted several times with dichloromethane. The combined extracts are dried over sodium sulfate and concentrated to yield eight grams of crude product. The solid product is recrystallized from cyclohexane to yield 5.9 g of (exo)-octahydro-5,8-epoxy-1H-benzopyran-3-ol, m.p. 101–103°.

EXAMPLE 6

[1R-(1α,2β(Z),3β,4α)]-7-[3-(Hydroxymethyl)-7-oxabicyclo-[2.2.1]hept-2-yl]-5-heptenoic acid (a) A mixture of N-acetylpyridinium chloride is prepared by adding 9.6 ml. (136 mmole) of acetyl chloride dropwise to 56 ml. of pyridine. To this is added 5.0 g. (27 mmole) of (exo)-3-(2-methoxyethenyl)-7-oxabicyclo[2.2.1]-heptane-2-methanol dissolved in 5 ml. of pyridine. The resulting mixture is stirred at room temperature for 1.5 hours and poured into brine. The product is extracted into ether (3×200 ml.), the ether extracts are washed with 5% hydrochloric acid (2×400 ml.) and brine (1×200 ml.) and dried over sodium sulfate. Concentration yields a yellow oil which is purified by passage through a short column of silica gel (150 ml.) with dichloromethane, yield 4.42 g. of an oil.

(b) To a solution of 4.42 g. (19.6 mmole) of the oil in 500 ml. of tetrahydrofuran containing 50 ml. of water is added 31.1 g. (97.8 mmole) of mercuric acetate. The yellow suspension which forms is stirred for 10 minutes and then the entire mixture is poured into a solution containing 200 g. of potassium iodide in 2 l. of water. Upon shaking, the yellow color disappears and the mixture is extracted with benzene (3×500 ml.). The combined benzene extracts are washed with potassium iodide solution and brine and dried over sodium sulfate. Concentration yields 3.7 g. of material which crystallizes on standing in an ice box.

(c) A Wittig reagent is prepared in dimethyl sulfoxide (dried over calcium hydride) by adding a solution of sodium methylsulfinylmethide (prepared by heating 300 mg. of sodium hydride in 60 ml. of dimethyl sulfoxide at 75° until hydrogen evolution stops) dropwise to a solution of 5.32 g. (12 mmole) of 4-carboxybutyl triphenylphosphonium bromide in 100 ml. of dimethyl sulfoxide. After the first orange color, lasting more than 10 seconds forms, an equivalent amount of base is added to form the ylide. To this deep orange solution is added a solution of the product of part (b) in 20 ml. of dimethyl slfoxide and the resulting mixture stirred at room temperature for 45 minutes. The reaction is quenched by addition of 24 mmole of acectic acid and the mixture poured into brine (300 ml.) and extracted with ether (3×200 ml.). Concentration of these extracts gives an oil which is stirred with saturated sodium bicarbonate solution until crystalline triphenylphosphine oxide forms in the mixture. This mixture is washed with benzene and acidified with 10% hydrochloric acid. The aqueous layer is saturated with salt and extracted with ether which on drying (sodium sulfate) and concentration gives 2.43 g. of crude product. The mixture is stirred 24 hours with 10% aqueous sodium hydroxide and reisolated by acidification and ether extraction. The product is purified on 500 g. of silica gel with 50/50 ethyl acetate-hexane as the eluant which gives 600 mg. of acid which crystallizes on standing. This is recrystallized twice from ethyl acetate-cyclohexane to yield 320 mg. of [1R-(1α,2β(Z), 3β,4α)]-7-[3-(hydroxymethyl)-7-oxabicyclo[2.2.1]hept-2-yl]-5-heptenoic acid, m.p. 59°–63°.

EXAMPLE 7

[1R-(1α,2β(5Z),3β,4α)]-7-[3-(hydroxymethyl)-7-oxabicyclo[2.2.1]hept-2-yl]-5-heptenoic acid, methyl ester A solution of diazomethane in ether is prepared from 3 g. of N-methylnitro-nitrosoguanidine in 50 ml. of ether with dropwise addition at 0° of 9 ml. of 40% potassium hydroxide/water solution. This solution (dried over potassium hydroxide pellets) is added dropwise to a stirring solution of [1R-(1α,2β(Z), 3β,4α)]-7-[3-(hydroxymethyl)-7-oxabicyclo[2.2.1]hept-1-yl]-5-heptenoic acid (254 g., 10 mmole in ether (150 ml.) over a ten minute period. Stirring is continued for one hour. The excess diazomethane is destroyed by the addition of acetic acid (1.5 ml.). The solution is washed with 5% sodium bicarbonate solution, brine, dried over sodium sulfate, and concentrated in vacuo to yield 2.6 g. of product (one spot by TLC — silica gel; ethyl acetate; $R_f$=0.5). The residue is chromatographed on silica gel (200 ml.) eluting with 1) ethyl acetate/pentane (1:9), 2) ethyl acetate/pentane (1:4), and 3) ethyl acetate/pentane (2:3) to yield 2.23 g. of [1R-(1α,2β(5Z), 3β,4α)]-7-[3-(hydroxymethyl)-7-oxabicyclo[2.2.1]hept-2-yl]-5-heptenoic acid, methyl ester as an oil.

EXAMPLE 8

[1R-(1α,2β(5Z),3β,4α)]-7-[3-formyl-7-oxabicyclo[2.2.1]hept-2-yl]-5-heptenoic acid, methyl ester A solution of chromium trioxide/pyridine is prepared in anhydrous dichloromethane (from 5.38 g, 54 mmoles of chromium trioxide, 8.7 ml., 108 mmoles of pyridine and 200 ml. of dichloromethane) and stirred at room temperature for twenty minutes. Eight grams of dry Celite (diatomaceous earth dried at 100° overnight) are then added followed by a solution of [1R-(1α,2β(5Z),3β,4α)]-7-[3-(hydroxymethyl)-7-oxabicyclo[2.2.1]hept-2-yl]-5-heptenoic acid, methyl ester (2.38 g., 8.94 mmoles in 15 ml. of dichloromethane). The resulting mixture is stirred under nitrogen for fifteen minutes and then filtered. The filtrate is washed with 5% sodium bicarbonate solution (2 × 100 ml.), 10% hydrochloric acid (2 × 100 ml.), 5% sodium bicarbonate solution (2×100 ml.), water (1×200 ml.) and brine (2×100 ml.). After drying over sodium sulfate, the dichloromethane solution is concentrated in vacuo to yield 2.6 g. of crude product. The crude product is purified is purified by column chromatography on Silicar CC-7 silica gel (300 ml.) eluting with 10% ethyl acetate/hexane to yield 2.1 g. of [1R-(1α,2β(5Z),3β,4α)]-7-[3-formyl-7-oxabicyclo[2.2.1]hept-2-yl]-5-heptenoic acid, methyl ester as an oil.

EXAMPLE 9

[1R-(1α,2β(5Z),3β(1E),4α]-7-[3-(3-oxo-1-octenyl)-7-oxabicyclo[2.2.1]hept-2-yl]-5-heptenoic acid, methyl ester A solution of [1R-(1α,2β(5Z),3β,4α)]-7-[3-formyl-7-oxabicyclo[2.2.1]hept-2-yl]-5-heptenoic acid, methyl ester (1.18 g., 0.0044 moles) and tributyl-2-oxoheptylidenephosphorane (1 g., 0.0044 moles) in anhydrous ether (50 ml.) is heated at reflux for three days. The reaction mixture is concentrated in vacuo. The residue is purified by column chromatography on Silicar CC-7 silica gel eluting with 5% ethyl acetate/chloroform to yield 1.3 g. of oil. The oil is dissolved in pentane (25 ml.) and chilled to yield 1.2 g. of [1R-(1α,2β(5Z),3β(1E),-4α)]-7-[3-(3-oxo-1-octenyl)-7-oxabicyclo[2.2.1]hept-2yl]-5-heptenoic acid, methyl ester, m.p. 32°-34°.

EXAMPLE 10

[1R-(1α,2β(5Z),3β(1E,3R*),4α)]-7-[3-(3-hydroxy-1-octenyl)-7-oxabicyclo[2.2.1]hept-2-yl]-5-heptenoic acid, methyl ester and

[1R-(1α,2β(5Z),3β(1E,3S*), 4β)]-7-[3-(3-hydroxy-1-octenyl)-7-oxabicyclo[2.2.1]hept-2-yl]-5-heptenoic acid, methyl ester A solution of [1R-(1α,2β(5Z),3β(1E),4α)]-7-[3-(3-oxo-1-octenyl)-7-oxabicyclo[2.2.1]hept-2-yl]-5-heptenoic acid, methyl ester (1.26 g., 0.0035 moles) in anhydrous dimethoxyethane(20 ml.) is chilled to −78° and treated dropwise with a solution of lithium tri-sec. butylborohydride (3.8 ml., 0.0038 moles) over two minutes. The reaction mixture is stirred at −78° for 30 minutes. The reaction mixture is then quenched with saturated ammonium chloride solution (10 ml.) and extracted several times with ethyl acetate (3×100 ml.). The combined ethyl acetate extracts are dried over magnesium sulfate and concentrated in vacuo. The residue is purified on a 1" × 24" silica gel column eluting with (1) benzene, (2) 2.5% ethyl acetate/benzene and (3) 5% ethyl acetate/benzene to yield 550 mg. of (a) [1R-(1α,2β(5Z), 3β(1E,3R*),4β)]-7-[3-(3-hydroxy-1-octenyl)-7-oxabicyclo]2.2.1]hept-2-yl]-5-heptenoic acid, methyl ester and 370 mg. of (b) [1R-)1α,2β(5Z),3β(-1E,3S*),4α)]-7-[3-(3-hydroxy-1-octenyl)-7-oxabicyclo[2.2.1]hept-2-yl]-5-heptenoic acid.

a. Analysis Calc'd. for $C_{22}H_{36}O_4$: C, 72.49; H, 9.96. Found: C, 72.24; H, 10.01.

b. Analysis Calc'd. for $C_{22}H_{36}O_4$: C, 72.49; H, 9.96. Found: C, 72.22; H, 9.92.

EXAMPLE 11

[1R-(1α,2β(5Z),3β(1E,3R*),4α)]-7-[3-(3-hydroxy-1-octenyl)-7-oxabicyclo[2.2.1]hept-2-yl]-5-heptenoic acid and

[1R-(1α,2β(5Z),3β(1E,3S*),4α)]-7-[3-(3-hydroxy-1-octenyl)-7-oxabicyclo[2.2.1]hept-2-yl]-5-heptenoic acid (a) A solution of chromium trioxide/pyridine is prepared in anhydrous dichloromethane (from 5.9 g., 59 mmole, of chromium trioxide, 9.5 ml. 118 mmole, of pyridine and 200 ml. of dichloromethane) and stirred at room temperature for 25 minutes. Eight grams of dry Celite (dried at 100° overnight) is then added followed by 2.61 g. (9.8 mmole) of [1R-(1α,2β(5Z),3β,4α)]-7-[3-(hydroxymethyl)-7-oxabicyclo[2.2.1]hept-2-yl]-5-heptenoic acid, methyl ester dissolved in 5 ml. of dichloromethane. The resulting mixture is stirred under nitrogen for 15 minutes and then worked up. The Celite-chromium trioxide mixture is removed by filtration and the filtrate is washed sequentially with saturated sodium bicarbonate solution (2×100 ml.), water (200 ml.) and brine (100 ml.). After drying over sodium sulfate, the mixture is concentrated under vacuum to give 2.34 g. of [1R-(1α,2β(5Z),3β,4α)]-7-[3-formyl-7 -oxabicyclo[2.2.1]hept-2-yl]-5-heptenoic acid, methyl ester.

(b) A mixture of Horner-Wittig reagent is prepared from sodium hydride (washed free of oil with hexane) (470 mg., 9.8 mmole) and dimethyl(2-oxoheptyl)phosphonate (1.82 g., 8.2 mmole) in dry dimethoxyethane (175 ml.). After combining these reagents, stirring is continued under nitrogen for 30 minutes during which time a white paste-like material forms. A solution of the product of part a (2.09 g., 8.2 mmole) in dimethoxyethane (40 ml.) is added and stirring continued for three hours during which time the mixture becomes homogeneous and yellow. The solvent is then removed under vacuum and the residue partitioned between ether and saturated sodium bicarbonate solution. The ether layer is washed with brine, dried over sodium sulfate and concentrated to yield 3.4 g. of crude material. This is purified by HPLC chromatography on a 1" by 24" column of silica gel using 0.5% ethyl acetate/benzene as the eluant. This yields 0.79 g. of pure [1R-(1α,2β(5Z),3β(1E),4α)]-7-[3-(3-oxo-1-octenyl)-7-oxabicyclo[2.2.1]hept-2-yl]-5-heptenoic acid, methyl ester and 1.67 g. of mixed fractions. The mixed fractions are rechromatographed on the same column with 30% hexane/benzene as the eluant yielding an additional 0.83 g. of pure trans-ketone. The pure fractions are combined for a total yield of 1.62 g.

(c) A solution of lithium tri-sec.butylborohydride (3.8 ml., 3.8 mmole) is added dropwise under nitrogen to a solution of the product of part (b) (1.26 g., 3.5 mmole) in 15 ml. of dry dimethoxyethane at −78°. The reaction is allowed to proceed at −78° for 30 minutes and then quenched by the addition of 9 ml. of saturated ammonium chloride solution. The mixture is then poured into brine (20 ml.) and extracted with ethyl acetate. The extracts are washed with ethanolamine-water solution (50/50) to remove borane side products, then dried over magnesium sulfate and concentrated to yield the crude product. The two diastereomers are separated by HPLC on a silica gel column (1"×24") using 2.5% ethyl acetate/benzene to elute the less polar isomer (β—OH) and 5% ethyl acetate/benzene to elute the more polar isomer (α—OH). In this way 449 mg. of [1R-(1α,2β(5Z),3β(1E,3R*),4α)]-7-[3-(3-hydroxy-1-octenyl)-7-oxabicyclo[2.2.1]-hept-2-yl]-5-heptenoic acid, methyl ester (β—OH isomer) and 300 mg. of [1R-(1α,2β(5Z),3β(1E,3S*),4α)]-7-[3-(3-hydroxy-1-octenyl)-7-oxabicyclo[2.2.1]hept-2-yl]-5-heptenoic acid, methyl ester (α—OH isomer) are obtained.

(d) A mixture of the β—OH isomer from part c (449 mg., 1.2 mmole) in tetrahydrofuran (65 ml.) and water (13 ml.) and lithium hydroxide-water (504 mg., 12 mmole) in water (13 ml.) is prepared and stirred at 0° under nitrogen for three hours, then kept at 0° overnight. During this time the mixture becomes homogenous and is acidified to pH3 with a 10% oxalic acid solution. The mixture is saturated with salt and extracted with ether (3×100 ml.). The ether extracts are dried over sodium sulfate and concentrated yielding an oil containing water. This is dried by solution in dichloromethane and drying over sodium sulfate. Removal of the solvents under vacuum yields 425 mg. of crude acid. This is purified by dissolving in 10% potassium carbonate solution, treatment of this solution with carbon, acidification with hydrochloric acid and re-extraction with ether. Removal of the solvent gives 302 mg. of [1R-(1α,2β(5Z),3β(1E,3R*),4α)]-7-[3-(3-hydroxy-1-octenyl)-7-oxabicyclo[2.2.1]hept-2-yl]-5-heptenoic acid as an oil.

Analysis calc'd: C, 71.96; H, 9.78. Found: C, 71.85; H, 9.66.

(e) A mixture of the β—OH isomer from part c (398 mg., 1.1 mmole) in tetrahydrofuran (60 ml.) and water (12 ml.) and lithium hydroxide/water (462 mg., 11 mmoles) in water (12 ml.) is prepared and stirred at room temperature for three hours. The mixture is diluted with brine (100 ml.) and acidified to pH 3 with 10% hydrochloric acid solution. The product is removed by extraction with ether. The ether extracts are dried over magnesium sulfate and concentrated to yield the crude acid. This is purified by dissolving in dilute potassium carbonate, washing the aqueous layer with pentane and acidifying with dilute hydrochloric acid followed by extraction with ether as before. The purified material is dried under vacuum over phosphorus pentoxide at room temperature for five days to yield 100 mg. of [1R-(1α,2β(5Z),3β(1E,3S*),4α)]-7-[3-(3-hydroxy-1-octenyl)-7-oxabicyclo[2.2.1]hept-2-yl]-5-heptenoic acid.

Analysis Calc'd. for $C_{21}H_{34}O_4$: C, 71.96; H, 9.78. Found: C, 71.68; H, 9.49.

EXAMPLE 12

[1R-(endo,cis)]-7-Oxabicyclo[2.2.1]hept-5-ene-2,3-dicarboxylic acid

A solution of maleic acid (982 g., 8.5 moles) in water (2100 ml.) is treated with furan (618 ml., 8.5 moles) and stirred at room temperature in a sealed flask for forty-eight hours. The unreacted furan is removed and the aqueous solution treated with charcoal and filtered. The filtrate is chilled in the refrigerator overnight. The resultant precipitate is collected by filtration and dried over phosphorus pentoxide to yield 250 g. of [1R-(endo,cis)]-7-oxabicyclo[2.2.1]hept-5-ene-2,3-dicarboxylic acid, m.p. 149°–150°.

EXAMPLE 13

(endo)-3a,4,7,7a-Tetrahydro-4,7-epoxyisobenzofuran-1(3H)-one

Trifluoroacetic anhydride (90 ml.) is chilled to 0° and treated with [1R-(endo,cis)]-7-oxabicyclo[2.2.1]hept-5-ene-2,3-dicarboxylic acid (10 g., 0.0543 moles). The slurry is stirred at 0° until solution occurs (~10 minutes). The mixture is then concentrated in vacuo at 0°. The resultant solid is added to a slurry of sodium borohydride (2.35 g., 0.062 moles) in tetrahydrofuran (250 ml.) at 0°. The reaction mixture is then stirred at room temperature for two hours. The mixture is concentrated in vacuo. The solid residue is chilled in an ice bath and treated dropwise with 75 ml. of 10% hydrochloric acid. The mixture is then extracted with dichloromethane (3×200 ml.). The combined dichloromethane extracts are washed with 5% sodium bicarbonate solution, dried over sodium sulfate, and concentrated in vacuo to yield 3.3 g. of (endo)-3a,4,7,7a-tetrahydro-4,7 epoxyisobenzofuran-1(3H)-one which is recrystallized from benzene/pentane to yield 2.1 g., m.p. 121°.

EXAMPLE 14

(endo)-1,3,3a,4,7,7a-Hexahydro-4,7-epoxyisobenzofuran-1-ol

A solution of (endo)-3a,4,7,7a-tetrahydro-4,7-epoxyisobenzofuran-1(3H)-one (3 g., 0.0197 moles) in toluene (100 ml.) is chilled to −78° and treated dropwise over five minutes with a solution of diisobutyl aluminum hydride in toluene (26.3 ml., 0.0395 moles). The reaction mixture is stirred at −78° for 20 minutes then quenched with the dropwise addition of 10% acetic acid (20 ml.). The reaction mixture is allowed to warm to room temperature. The mixture is poured into 50 ml. of 10% hydrochloric acid and extracted with dichloromethane (7×200 ml.). The combined dichloromethane extracts are washed with saturated sodium bicarbonate solution, dried over sodium sulfate and concentrated in vacuo. The residue is chromatographed on Silicar CC-7 (200 ml. silica gel) eluting with 10% ethyl acetated dichloromethane to yield 1.6 g. of product which is recrystallized from benzene/pentane to yield 1.5 g. of (endo)-1,3,3a,4,7,7a-hexahydro-4,7-epoxyisobenzofuran-1-ol, m.p. 108°–110°.

EXAMPLE 15

(ends)-3-(2-Methoxyethenyl)-7-oxabicyclo[2.2.1]Hept-5-ene-2-methanol

By substituting (endo)-1,3,3a-hexahydro-4,7-epoxyisobenzofuran-1-ol in the procedure of Example 4, (endo)-3-(2-methoxyethenyl)-7-oxabicyclo[2.2.1]hept-5-ene-2-methanol is obtained.

EXAMPLE 16

(endo)-3,4,4a,5,7,7a-Hexahydro-5,8-epoxy-1H-benzopyran-1-ol

By substituting (endo)-3-2-methoxyethenyl)-7-oxabicyclo[2.2.1]hept-5-ene-2-methanol in the procedure of Example 5, (endo)-3,4,4a,5,7,7a-hexahydro-5,8-epoxy-1H-benzopyran-1-ol is obtained.

EXAMPLE 17

[1R-(1α,2α(Z), 3α,4α)]-7-(3-Hydroxymethyl)-7-oxabicyclo[2.2.1]-hept-5-en-2-yl]-5-heptenoic acid By substituting (endo)-3-(2-methoxyethenyl)-7-oxabicyclo[2.2.1]hept-5-ene-2-methanol in the procedure of Example 6, [1R-(1α,2α(Z),3α,4α)]-7-(3-hydroxymethyl)-7-oxabicyclo[2.21]hept-5-en-2-yl]-5-heptenoic acid is obtained.

EXAMPLE 18

[1R-(1α,2α(Z), 3α,4α)]-7-(3-Hydroxymethyl)-7-oxabicyclo[2.2.1]hept-5-en-2-yl]-5-heptenoic acid, methyl ester By substituting [1R-(1α,2α(Z),3α, 4α)]-7-oxabicyclo[2.2.1]hept-5-en-2-yl]-5-heptenoic acid in the procedure of Example 7, [1R-(1α,2α(Z),3α,4α)]-7-(3-hydroxymethyl)-7-oxabicyclo[2.2.1]hept-5-en-2-yl]-5-heptenoic acid, methyl ester is obtained.

EXAMPLE 19

[1R-(1α,2α(5Z),3α,4α)]-7-(3-formyl)-7-oxabicyclo[2.2.1]hept-5-en-2-yl]-5-heptenoic acid, methyl ester By substituting [1R-(1α,2α(Z), 3α,4α)]-7-(hydroxymethyl)-7-oxabicyclo[2.2.1]hept-5-en-2-yl]-5-heptenoic acid, methyl ester in the procedure of Example 8, [1R-(1α,2α(5Z),3α,4α)]-7-(3-formyl)-7-oxabicyclo[2.2.1]hept-5-en-2-yl]-5-heptenoic acid, methyl ester is obtained.

EXAMPLE 20

[1R-(1α,2α(5Z),3α (1E), 4α]-7-[3-(3-oxo-1-octenyl)-7-oxabicyclo[2.2.1]hept-5-en-2-yl]-5-heptenoic acid, methyl ester By substituting [1R-(1α,2α(5Z), 3α,4α]-7-(3-formyl-7-oxabicyclo[2.2.1]hept-5-en-2-yl]-5-heptenoic acid, methyl ester in the procedure of Example 9, [1R-(1α,2α(5Z),3α(1E), 4α]-7-[3-(3-oxo-1-octenyl)-7-oxabicyclo[2.2.1]hept-5-en-2-yl]-5-heptenoic acid, methyl ester is obtained.

EXAMPLE 21

[1R-(1α,2α(5Z),3α(1E,3R*),4α)]-7-[3-(3-hydroxy-1-octenyl)-7-oxabicyclo[2.2.1]hept-5-en-2-yl]-5-heptenoic acid, methyl ester and
[1R-(1α,2α(5Z),3α(1E,3S*),4α)]-7-[3-(3-hydroxy-1-octenyl)-7-oxabicyclo[2.2.1]hept-5-en-2-yl]-5-heptenoic acid, methyl ester By substituting the product of Example 20 in the procedure of Example 10, [1R-(1α,2α(5Z),3α(1E,3R*)-,4α)]-7-[3-(3-hydroxy-1-octenyl)-7-oxabicyclo[2.2.1-]hept-5-en-2yl]-5-heptenoic acid, methyl ester and [1R-(1α,2α(5Z), 3α(1E,3S*),4α)]-7-[3-(3-hydroxy-1-octenyl)-7-oxabicyclo[2.2.1]-hept-5-en-2-yl]-5-heptenoic acid, methyl ester, respectively, are obtained.

EXAMPLE 22

[1R-(1α,2α(5Z),3α(1E,3R*),4α)]-7-[3-(3-hydroxy-1-octenyl)-7-oxabicyclo[2.2.1]hept-5-en-2-yl]-5-heptenoic acid and
[1R-(1α,2α(5Z),3α(1E,3S*),4α)]-7-[3-(3-hydroxy-1-octenyl)-7-oxabicyclo[2.2.1]hept-5-en-2-yl]-5-heptenoic acid By substituting the product of Example 20 in the procedure of Example 11 c and continuing as in parts d and e, [1R-(1α,2α(5Z),3α(1E,3R*),4α)]-7-[3-(3-hydroxy-1-octenyl)-7-oxabicyclo[2.2.1]hept-5-en-2-yl]-5-heptenoic acid and [1R,(1α,2α(5Z),3α(1E,3S*),4α)]-7-[3-(3-hydroxy-1-octenyl)-7-oxabicyclo[2.2.1]hept-5-en-2-yl]-5-heptenoic acid, respectively are obtained.

EXAMPLE 23

[1R-(endo,cis)]-7-Oxabicyclo[2.2.1]heptane-2,3-dicarboxylic acid

A slurry of [1R-(endo,cis)]-7-oxabicyclo[2.2.1]hept-5-ene-2,3-dicarboxylic acid (33.8 g., 0.18 moles), and 10% palladium/carbon (800 mg.) in absolute ethanol (1000 ml.) is stirred vigorously under one atmosphere of hydrogen until the uptake of hydrogen has ceased (4460 ml.). The reaction mixture is then filtered and the filtrate concentrated in vacuo to yield 34 g. of [1R-(endo,-cis)]-7-oxabicyclo[2.2.1]-heptane-2,3-dicarboxylic acid. An analytical sample is prepared by recrystallizing 3 g. of the diacid from ethyl acetate/pentane to yield 2.9 g., m.p. 169°–170°.

EXAMPLE 24

(endo)-Hexahydro-4,7-epoxyisobenzofuran-1,3-dione

A slurry of [1R-(endo,cis)]-7-oxabicyclo[2.2.1]heptane-2,3-dicarboxylic acid (8.4 g., 0.045 moles) in acetyl chloride (80 ml.) is heated at reflux for thirty minutes. The resultant solution is concentrated in vacuo. The resultant solid is recrystallized from benzene to yield 6 g. of (endo)-hexahydro-4,7-epoxyisobenzofuran-1,3-dione, m.p. 154°–155°.

EXAMPLE 25

(endo)-Hexahydro-4,7-epoxyisobenzofuran-1(3H)-one

Sodium borohydride (3.48 g., 0.092 moles) is slurried in anhydrous tetrahydrofuran (150 ml.), chilled to 0° and treated dropwise over ten minutes with a solution of (endo)-hexahydro-4,7-epoxyisobenzofuran-1,3-dione (14.8 g., 0.088 moles) in anhydrous tetrahydrofuran (250 ml.). The reaction mixture is stirred at room temperature for one hour, then concentrated in vacuo. The residue is chilled in an ice bath and treated dropwise with 10% hydrochloric acid (50 ml.). The mixture is diluted with brine (100 ml.) and extracted several times with dichloromethane (5×200 ml.). The combined dichloromethane extracts are dried over magnesium sulfate and concentrated in vacuo. The residue is dissolved in dichloromethane and filtered through silica gel. The filtrate is concentrated in vacuo. The residue is recrystallized from heptane to yield 6.8 g. of (endo)-hexahydro-4,7-epoxyisobenzofuran-1(3H)-one, m.p. 153°–155°.

EXAMPLE 26

(endo)-Octahydro-4,7-epoxyisobenzofuran-1-ol

A solution of (endo)-hexahydro-4,7-epoxyisobenzofuran-1(3H)-one (8.03 g., 0.052 moles) in anhydrous toluene (250 ml.) is chilled to −78° and treated dropwise over five minutes with a solution of diisobutyl aluminum hydride (70 ml., 0.105 moles) in toluene. The reaction mixture is stirred at −78° for twenty minutes. The reaction mixture is then quenched with 10% acetic acid (50 ml.) and allowed to come to room temperature. The mixture is treated with 10% hydrochloric acid (25 ml.) and extracted several times with dichloromethane (7×200 ml.). The combined dichloromethane extracts are dried over solid sodium bicarbonate and concentrated in vacuo. The solid residue is recrystallized from heptane to yield 7.5 g. of (endo)-octahydro-4,7-epoxyisobenzofuran-1-ol, m.p. 132°–133°.

EXAMPLE 27

(endo)-3-(2-Methoxyethenyl)-7-oxabicyclo[2.2.1]heptane-2-methanol

Lithium diisopropyl amide is prepared by dissolving diisopropyl amine (140 ml., 1.0 moles) in pentane (600 ml.), chilling the solution in an ice bath, and adding n-butyl lithium (311 ml. of 2.42M in hexane, 0.753 moles) dropwise over 15 minutes. The reaction mixture is concentrated in vacuo to yield the desired lithium diisopropyl amide which is then dissolved in anhydrous tetrahydrofuran (300 ml.) and added dropwise over ten minutes to a slurry of (methoxymethyl)-triphenylphosphonium chloride (259 g., 0.755 moles) in anhydrous toluene (3700 ml.) chilled in an ice bath. The dark red mixture is stirred at 4° for 15 minutes. (endo)-Octahydro-4,7-epoxyisobenzofuran-1-ol (39.2 g., 0.251 moles) is added and the reaction mixture stirred at room temperature for three hours. The reaction mixture is then poured into brine (2000 ml.) and treated with concentrated hydrochloric acid to pH 7. The mixture is extracted with ether (3×800 ml.). The combined ether extracts are dried over sodium sulfate and concentrated. The residue is dissolved in ether (1000 ml.) and chilled overnight. The precipitated phosphine oxide is removed and the ether solution concentrated in vacuo. The residue is chromatographed on silica gel (2000 ml.) eluting with (1) dichloromethane, (2) 10% ethyl acetate/dichloromethane and (3) 50% ethyl acetate/dichloromethane. The fractions containing the product are concentrated in vacuo. The resultant residue is distilled in vacuo to yield 17 g. of (endo)-3-(2-methoxyethenyl)-7-oxabicyclo-[2.2.1]heptane-2-methanol, b.p. 110°/0.001 mm.

EXAMPLE 28

(endo)-Octahydro-5,8-epoxy-1H-benzopyran-3-ol (endo)-3-(2-Methoxyethenyl)-7-oxabicyclo[2.2.1]heptane-2-methanol (2.3 g., 0.013 moles) is dissolved in cold 88% formic acid (25 ml.). The solution is stirred at room temperature for 30 minutes. The solution is then chilled in a salt/ice bath and treated dropwise with 10% sodium hydroxide to pH 7.0. The mixture is saturated with sodium chloride and extracted with dichloromethane (4×100 ml.). The combined organic extracts are dried over sodium sulfate and concentrated in vacuo. The residue is chromatographed on Silicar CC-7 (neutral silica gel) (200 ml.) eluting with (1) dichloromethane, (2) 5% ethyl acetate/dichloromethane, (3) 20% ethyl acetate/dichloromethane and (4) ethyl acetate. The fractions containing the desired hemiacetal are combined and concentrated. An analytical sample is obtained by distilling the residue in vacuo to yield 1 g. of (endo)-octahydro-5,8-epoxy-1H-benzopyran-3-ol, m.p. 37°–40°; b.p. 125°–130°/0.001 mm.

EXAMPLE 29

[1R-(1α,2α(Z),3α,4α]-7-[3-(Hydroxymethyl)-7-oxabicyclo [2.2.1]hept-2-yl]-5-heptenoic acid A solution of (4-carboxybutyl)triphenylphosphonium bromide (9.17 g., 0.021 moles) in anhydrous dimethyl sulfoxide (80 ml.) is treated dropwise with dimsyl ion (from 0.1 moles of sodium hydride in 60 ml. of dimethylsulfoxide heated at 75° until hydrogen evolution ceases) until an orange color persists. A second amount of dimsyl ion equaling the first is then added. The reaction mixture is stirred at room temperature for 15 minutes then treated with a solution of (endo)-octahydro-5,8-epoxy-1H-benzopyran-3-ol (1.76 g., 0.01 moles) in dimethyl sulfoxide (5 ml.). The reaction mixture is stirred at room temperature for one hour then quenched by the dropwise addition of a solution of glacial acetic acid (1.7 g.) in ether (10 ml.). The reaction mixture is poured into brine (100 ml.), adjusted to pH 4 with 10% hydrochloric acid, and extracted with ether (4×100 ml.). The combined ether extracts are dried over sodium sulfate and concentrated. The residue is treated with 5% sodium bicarbonate solution (100 ml.) and stirred for 15 minutes. The mixture is then extracted with benzene (10×50 ml.), acidified with 10% hydrochloric acid, saturated with sodium chloride, and extracted with ether (4×100 ml.).

The combined ether extracts are dried over sodium sulfate and concentrated. The residue is dissolved in ether 25 ml.) and chilled overnight. The resultant phosphine oxide is removed by filtration. The filtrate is concentrated in vacuo. The residue is dissolved in 10 ml. of ethyl acetate and treated with dicyclohexylamine until basic. The resultant solid is recrystallized from ethyl acetate. The precipitate is filtered, dissolved in water, acidified with 10% hydrochloric acid and extracted with ethyl acetate. The ethyl acetate extract is dried over sodium sulfate and concentrated. The residue is chromatographed on Silicar CC-7 (100 ml.) (neutral silica gel, pH 7) eluting with ethyl acetate to yield 2 g. of [1R-(1α,2α(Z),3α,4α]-7-[3-(hydroxymethyl)-7-oxabicyclo[2.2.1]hept-2-yl]-5-heptenoic acid.

Analysis Calc'd. for $C_{14}H_{22}O_4$: C, 66.12; H, 8.72. Found: C, 66.23; H, 8.60.

EXAMPLE 30

[1R-(1α,2α(Z),3α,4α)]-7-(3-Hydroxymethyl)-7-oxabicyclo[2.2.1]hept-2-yl]-5-heptenoic acid, methyl ester By substituting [1R-(1α,2α(Z), 3α,4α)]-7-oxabicyclo[2.2.1]hept-2-yl]-5-heptenoic acid in the procedure of Example 7, [1R-(1α,2α(Z),3α,4α)]-7-(3-hydroxyme-

EXAMPLE 31

[1R-[1α,2α(5Z), 3α,4α)]-7-(3-formyl)-7-oxabicyclo[2.2.1]hept-2-yl]-5-heptenoic acid, methyl ester By substituting [1R-(1α,2α(Z),3α,4α)]-7-(hydroxymethyl)-7-oxabicyclo[2.2.1]hept-2-yl]-5-heptenoic acid, methyl ester in the procedure of Example 8, [1R-[1α,2α(5Z),3α,4α)]-7-(3-formyl)-7-oxabicyclo[2.2.1]hept-2-yl]-5-heptenoic acid, methyl ester is obtained.

EXAMPLE 32

[1R-(1α,2α(5Z), 3α(1E),4α]-7-[3-(3-oxo-1-octenyl)-7-oxabicyclo[2.2.1]hept-2-yl]-5-heptenoic acid, methyl ester By substituting [1R-(1α,2α(5Z),3α,4α]-7-(3-formyl-7-oxabicyclo[2.2.1]hept-2-yl)-5-heptenoic acid, methyl ester in the procedure of Example 9, [1R-(1α,2α(5Z),3α(1E),4α]-7-[3-(3-oxo-1-octenyl)-7-oxatricyclo[2.2.1]hept-2-yl]-5-heptenoic acid, methyl ester is obtained.

EXAMPLE 33

[1R-(1α,2α(5Z),3α(1E,3R*),4α)]-7-[3-(3-hydroxy-1-octenyl)-7-oxabicyclo[2.2.1]hept-2-yl]-5-heptenoic acid, methyl ester and

[1R-(1α,2α(5Z),3α(1E,3S*),4α)]-7-[3-(3-hydroxy-1-octenyl)-7-oxabicyclo[2.2.1]hept-2-yl]-5-heptenoic acid, methyl ester By substituting the product of Example 20 in the procedure of Example 10, [1R-(1α,2α(5Z),3α(1E,3R*)-,4α)]-7-[3-(3-hydroxy-1-octenyl-7-oxabicyclo[2.2.1-]hept-2yl]-5-heptenoic acid, methyl ester and [1R-(1α,-2α(5Z), 3α(1E,3S*), 4α)]-7-[3-(3-hydroxy-1-octenyl)-7-oxabicyclo[2.2.1]hept-2-yl]-5-heptenoic acid, methyl ester, respectively, are obtained.

EXAMPLE 34

[1R-(1α,2α(5Z),3α(1E,3R*),4α]-7-[3-(3-hydroxy-1-octenyl)-7-oxabicyclo[2.2.1]hept-2-yl)-5-heptenoic acid and

[1R-(1α,2α(5Z),3α(1E,3S*),4α)]-7-[3-(3-hydroxy-1-octenyl)-7-oxabicyclo[2.2.1]hept-2-yl)-5-heptenoic acid By substituting the product of Example 20 in the procedure of Example 11c and continuing as in parts d and e, [1R-(1α,2α(5Z),3α(1E,3R*),4α)]-7-[3-(3-hydroxy-1-octenyl)-7-oxabicyclo[2.2.1]hept-2-yl]-5-heptenoic acid and [1R-(1α,2α(5Z),3α(1E,3S*),4α)]-7-[3-(3-hydroxy-1-octenyl)-7-oxabicyclo[2.2.1]hept-2-yl]-5-heptenoic acid, respectively are obtained.

What is claimed is:

1. A compound of the formula

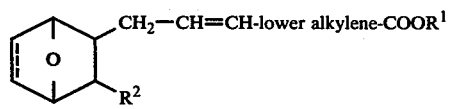

wherein
$R^1$ is hydrogen or lower alkyl;
$R^2$ is —CHO, —CH$_2$OH or —CH=CH—$R^3$— lower alkylene-CH$_3$;
$R^3$ is keto or hydroxymethyl; and the dotted line is an optional double bond;
said lower alkyl and lower alkylene groups having up to seven carbon atoms.

2. A compound as in claim 1 wherein $R^1$ is hydrogen or lower alkyl; $R^2$ is —CH$_2$OH or —CH=CH—$R^3$-lower alkylene-CH$_3$; and $R^3$ is hydroxymethyl.

3. A compound as in claim 1 wherein $R^2$ is —CH=CH—$R^3$-lower alkylene-CH$_3$.

4. A compound as in claim 1 wherein $R^2$ is —CH=CH—$R^3$-lower alkylene-CH$_3$; $R^3$ is hydroxymethyl and each lower alkylene group has 3 or 4 carbon atoms.

5. 7-[3-(3-hydroxy-1-octenyl)-7-oxabicyclo[2.2.1-]hept-2-yl]-5-heptenoic acid and $C_1$-$C_7$ lower alkyl esters thereof.

6. [1R-(1α,2β(5Z),3β(1E,3S*),4α)]-7-[3-(3-hydroxy-1-octenyl)-7-oxabicyclo[2.2.1]hept-2-yl]-5-heptenoic acid.

7. [1R-(1α,2β(5Z),3β(1E,3R*),4α)]-7-[3-(3-hydroxy-1-octenyl)-7-oxabicyclo[2.2.1]hept-2-yl]-5-heptenoic acid.

* * * * *

UNITED STATES PATENT AND TRADEMARK OFFICE
CERTIFICATE OF CORRECTION

PATENT NO. : 4,143,054
DATED : March 6, 1979
INVENTOR(S) : Peter W. Sprague

It is certified that error appears in the above-identified patent and that said Letters Patent are hereby corrected as shown below:

Title page, in the title delete "7-Oxadicycloheptene" and add -- 7-Oxabicycloheptene --.
Col. 2, line 54, delete the period after pyridine and add a comma.
Col. 2, line 57, delete "the" and add -- to --.
Col. 3, line 10, delete "X1" and add -- XI --.
Col. 8, line 46, delete "slfoxide" and add -- sulfoxide --.
Col. 10, line 10, delete "4β" and add -- 4α -- .
Col. 10, line 27, delete "4β" and add -- 4α --.
Col. 13, line 10, delete "(ends)" and add --(endo) --.
Col. 13, line 13, delete "1,3,3a-hexahydro-4,7-" and add -- 1,3,3a,4,7,7a-hexahydro-4,7- --.
Col. 13, line 21, delete 3-2-methoxyethenyl)- and add -- 3-(2-methoxyethenyl)- --.
Col. 13, line 34, delete "[2.21]" and add -- [2.2.1] -- .

Signed and Sealed this

First Day of April 1980

[SEAL]

Attest:

Attesting Officer

SIDNEY A. DIAMOND

Commissioner of Patents and Trademarks